US009600891B2

(12) United States Patent
Huang et al.

(10) Patent No.: US 9,600,891 B2
(45) Date of Patent: Mar. 21, 2017

(54) WEB BASED FAST QUERY VISUALIZATION OF TIME-VARYING MULTI-VARIATE VESSEL FLOW FIELD BY USING UNIFORM PARTITION STRATEGY

(71) Applicant: SIEMENS HEALTHCARE GMBH, Erlangen (DE)

(72) Inventors: Xiaoke Huang, Pittsburgh, PA (US); Jun Tao, Houghton, MI (US); Feng Qiu, Plainsboro, NJ (US); Daphne Yu, Yardley, PA (US)

(73) Assignee: Siemens Healthcare GmbH, Erlangen (DE)

( * ) Notice: Subject to any disclaimer, the term of this patent is extended or adjusted under 35 U.S.C. 154(b) by 102 days.

(21) Appl. No.: 14/508,527

(22) Filed: Oct. 7, 2014

(65) Prior Publication Data
US 2015/0097836 A1  Apr. 9, 2015

Related U.S. Application Data

(60) Provisional application No. 61/888,050, filed on Oct. 8, 2013.

(51) Int. Cl.
| | |
|---|---|
| *G06T 19/20* | (2011.01) |
| *G06T 7/00* | (2006.01) |
| *A61B 5/00* | (2006.01) |
| *G06F 17/50* | (2006.01) |
| *A61B 6/00* | (2006.01) |

(Continued)

(52) U.S. Cl.
CPC .......... *G06T 7/0081* (2013.01); *A61B 5/7425* (2013.01); *G06T 19/20* (2013.01); *A61B 5/026* (2013.01); *A61B 5/055* (2013.01); *A61B 6/504* (2013.01); *A61B 8/06* (2013.01); *A61B 2576/02* (2013.01); *G06F 17/5009* (2013.01)

(58) Field of Classification Search
None
See application file for complete search history.

(56) References Cited

U.S. PATENT DOCUMENTS

| | | | |
|---|---|---|---|
| 2006/0103678 A1* | 5/2006 | Cathier | G06T 19/00 345/649 |
| 2011/0190632 A1* | 8/2011 | Kim | A61B 8/14 600/443 |
| 2013/0038605 A1* | 2/2013 | Li | G06T 19/00 345/419 |

OTHER PUBLICATIONS

Bühler, K., Felkel, P., & La Cruz, A. (2004). Geometric methods for vessel visualization and quantification—a survey (pp. 399-419). Springer Berlin Heidelberg.*

(Continued)

*Primary Examiner* — Ryan D McCulley

(57) ABSTRACT

A method for visualizing flow data from computation fluid dynamics (CFD) applications in 2-dimensions (2D) includes receiving a 3-dimensional (3D) image volume from a CFD simulation of fluids flowing through vessels in a patient that is a snapshot of a fluid flow in the vessels at a certain time, subdividing the 3D image volume into 3D data blocks, minimizing a sum over a matrix of energy interactions defined for each pair of data blocks in the 3D image volume, where the minimization preserves a local shape of the vessels, where minimizing the sum over the matrix of energy interactions is performed on a graphics processing unit (GPU), and using the minimized energy interaction matrix to display on a monitor a 2D sketch of the 3D image volume, where the 2D sketch is displayed in real-time with respect to the time scale of the CFD simulation.

22 Claims, 9 Drawing Sheets

(a)

(b)

(51) Int. Cl.
  *A61B 8/06*  (2006.01)
  *A61B 5/026*  (2006.01)
  *A61B 5/055*  (2006.01)

(56) References Cited

OTHER PUBLICATIONS

Groher, M., Zikic, D., & Navab, N. (2009). Deformable 2D-3D registration of vascular structures in a one view scenario. Medical Imaging, IEEE Transactions on, 28(6), 847-860.*
Hauser, H. (2005). Toward new grounds in visualization. ACM SIGGRAPH Computer Graphics, 39(2), 5-8.*
Kanitsar, A., Fleischmann, D., Wegenkittl, R., Felkel, P., & Gröller, M. E. (2002). CPR—curved planar reformation (pp. 37-44). IEEE.*
Kanitsar, A., Wegenkittl, R., Fleischmann, D., & Groller, M. E. (Oct. 2003). Advanced curved planar reformation: Flattening of vascular structures. In Proceedings of the 14th IEEE Visualization 2003 (VIS'03) (p. 7). IEEE Computer Society.*
Preim, B., & Oeltze, S. (2008). 3D visualization of vasculature: an overview. In Visualization in medicine and life sciences (pp. 39-59). Springer Berlin Heidelberg.*
Saroul, L. (2006). Surface extraction and flattening for anatomical visualization (Doctoral dissertation, Université de Saint-Etienne, France).*
Won, J. H., Jeon, Y., Rosenberg, J. K., Yoon, S., Rubin, G. D., & Napel, S. (2013). Uncluttered single-image visualization of vascular structures using GPU and integer programming. Visualization and Computer Graphics, IEEE Transactions on, 19(1), 81-93.*
Won, J. H., Rubin, G. D., & Napel, S. (Aug. 2006). Flattening the abdominal aortic tree for effective visualization. In Engineering in Medicine and Biology Society, 2006. EMBS'06. 28th Annual International Conference of the IEEE (pp. 3345-3348). IEEE.*

* cited by examiner

WEB BASED FAST QUERY VISUALIZATION OF TIME-VARYING MULTI-VARIATE VESSEL FLOW FIELD BY USING UNIFORM PARTITION STRATEGY

CROSS REFERENCE TO RELATED UNITED STATES APPLICATIONS

This application claims priority from "Web Based Fast Query Visualization Of Time-Varying Multi-Variate Vessel Flow Field By Using Uniform Partition Strategy", U.S. Provisional Application No. 61/888,050 of Huang, et al., filed Oct. 8, 2013, the contents of which are herein incorporated by reference in their entirety.

TECHNICAL FIELD

This disclosure is directed to methods and systems for visualizing fluid flow in vessels in medical images.

DISCUSSION OF THE RELATED ART

Flow visualization is the study of methods to display dynamic behavior in liquids and gases. The field dates back to at least the mid-1400's, where Leonardo Da Vinci sketched images of fine particles of sand and wood shavings which had been dropped into flowing liquids. Since then, laboratory flow visualization has become more and more exact, with careful control of the particulate size and distribution. Advances in photography have also helped extend our understanding of how fluids flow under various circumstances.

More recently, the techniques of computational fluid dynamics (CFD) have extended the abilities of scientists to study flow by creating simulations of dynamic behavior of fluids under a wide range of conditions. The result of this analysis is usually a 2-dimensional (2D) or 3-dimensional (3D) grid of velocity vectors, which may be uniformly or non-uniformly spaced. The goal is then to analyze this vector field to identify features such as turbulence, vortices, and other forms of structure.

The vessel flow patterns in the human body are complex and challenging to visualize using conventional 2D modalities. Visualization of vessel data is an important preprocessing step in diagnosis of vascular diseases, monitoring, surgery planning, blood flow simulation, education and training of surgeons. To effectively visualize the vessels, removing the bones and other irrelevant detail is useful. However, some thin vessels with low intensity will be eliminated, which causes the formation of islands of vessels in the final rendering result. Moreover, due to the complex vascular structure of the vessels, abnormal features, such as aneurisms, may not be easy to identify in the visualization.

There are currently several unsteady flow visualization systems. However, although these systems can visualize unsteady flow data, the size of the flow data is often limited and some systems do not provide adaptive time step in particle integration. Furthermore, many of them do not allow particle integration in flow fields with moving grids.

A web-based application is any application that can use a web browser as a client. It does not require any complex roll out procedure to be deployed, and can also provide cross-platform compatibility in most cases, such as Windows, Mac OS, Linux, etc., because these application can operate within a web browser window. However, web-based applications have not yet been used for vessel flow visualization.

SUMMARY

Exemplary embodiments of the disclosure as described herein are directed to methods for querying and highlighting particles in a flow field by a Cross filter and a Boolean filter. A mapping approach according to an embodiment of the disclosure may map 3D vessels to 2D vessels and preserved the local shape of vessels. Performance may be optimized by a parallel implementation on a graphics processing unit (GPU), which can achieve an instantaneous query response even for a large number of particles, which can present users with more information of and be interactive with the flow field.

According to an embodiment of the disclosure, there is provided a method for visualizing flow data from computation fluid dynamics (CFD) applications in 2-dimensions (2D), the method including receiving a 3-dimensional (3D) image volume from a CFD simulation of fluids flowing through vessels in a patient that is a snapshot of a fluid flow in the vessels at a certain time, subdividing the 3D image volume into 3D data blocks, minimizing a sum over a matrix of energy interactions defined for each pair of data blocks in the 3D image volume, where the minimization preserves a local shape of the vessels, where minimizing the sum over the matrix of energy interactions is performed on a graphics processing unit (GPU), and using the minimized energy interaction matrix to display on a monitor a 2D sketch of the 3D image volume, where the 2D sketch is displayed in real-time with respect to the time scale of the CFD simulation.

According to a further embodiment of the disclosure, the method includes loading the 3D data blocks into memory of a web application for display, where the web application is accessible over the World Wide Web.

According to a further embodiment of the disclosure, the method includes distinguishing non-empty 3D data blocks that contain vessels from empty 3D data blocks that do not contain vessels, and only loading the non-empty 3D data blocks.

According to a further embodiment of the disclosure, the method includes calculating two look-up-tables (LUTs) when loading the non-empty data blocks, where the matrix of energy interactions is defined for each pair of non-empty data blocks.

According to a further embodiment of the disclosure, a first LUT is a mapping from a descriptor of the 3D image volume to an index that indicates a starting position in memory of the 3D image volume, and a second LUT indicates a memory position of each 3D data block of the image of the 3D image volume.

According to a further embodiment of the disclosure, the method includes receiving a selection of particles selected from the 2D sketch, and calculating and displaying statistical information about the selected particles.

According to a further embodiment of the disclosure, the information includes one or more of velocity, vorticity, wall shear stress, inlet and pressure.

According to a further embodiment of the disclosure, the selection is performed using a Cross filter.

According to a further embodiment of the disclosure, the selection is performed using a Boolean filter.

According to a further embodiment of the disclosure, the vessels are at least a part of a cardiovascular system of the patient.

According to a further embodiment of the disclosure, minimizing the sum over the matrix of energy interactions comprises minimizing $E=\sqrt{\Sigma_{i,j}(AV-T)_{ij}^2}$, where T is a column vector $\{t_{ij}|i,j \text{ in } [1,n]\}$, where $|v_i-v_j|=t_{ij}$, $v_i$ and $v_j$ are 2D positions of target block$_i$ and block$_j$, respectively, and $t_{ij}$ is a target distance, V is a column vector $\{v_1, \ldots, v_n\}$, and n is a number of block pairs, where the minimization is performed by varying the target positions $v_i$ and $v_j$.

According to a further embodiment of the disclosure, the method includes weighting elements of AV–T by a weight $W_n$ if a separation distance between block$_i$ and block$_j$ in 3D is less than a threshold distance, and by a weight $W_{nn}$ if the separation distance between block$_i$ and block$_j$ in 3D is greater than or equal to the threshold distance, where $W_n > W_{nn}$.

According to another embodiment of the disclosure, there is provided a method for visualizing flow data from computation fluid dynamics (CFD) applications in 2-dimensions (2D), including subdividing a 3-dimensional (3D) image volume into 3D data blocks, minimizing a sum over a matrix of energy interactions defined for each pair of data blocks in the 3D image volume by minimizing $E=\sqrt{\Sigma_{i,j}(AV-T)_{ij}^2}$, where T is a column vector $\{t_{ij}|i,j \text{ in } [1,n]\}$, where $|v_i-v_j|=t_{ij}$, $v_i$ and $v_j$ are 2D positions of target block$_i$ and block$_j$, respectively, and $t_{ij}$ is a target distance, V is a column vector $\{v_1, \ldots, v_n\}$, and n is a number of block pairs, where the minimization is performed by varying the target positions $v_i$ and $v_j$, and using the minimized energy interaction matrix to display on a monitor a 2D sketch of the 3D image volume.

According to a further embodiment of the disclosure, the method includes receiving the 3D image volume from a CFD simulation of fluids flowing through vessels in a patient that is a snapshot of a fluid flow in the vessels at a certain time, where the minimization preserves a local shape of the vessels, and where the 2D sketch is displayed in real-time with respect to the time scale of the CFD simulation.

According to a further embodiment of the disclosure, the method includes weighting elements of AV–T by a weight $W_n$ if a separation distance between block$_i$ and block$_j$ in 3D is less than a threshold distance, and by a weight $W_{nn}$ if the separation distance between block$_i$ and block$_j$ in 3D is greater than or equal to the threshold distance, where $W_n > W_{nn}$.

According to a further embodiment of the disclosure, minimizing the sum over the matrix of energy interactions is performed on a graphics processing unit (GPU).

According to an embodiment of the disclosure, there is provided a non-transitory program storage device readable by a computer, tangibly embodying a program of instructions executed by the computer to perform the method steps for visualizing flow data from computation fluid dynamics (CFD) applications in 2-dimensions (2D).

DETAILED DESCRIPTION OF EXEMPLARY EMBODIMENTS

Exemplary embodiments of the disclosure as described herein generally include systems and methods for a web based fast query visualization of a time-varying multi-variate vessel flow field. Accordingly, while the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

As used herein, the term "image" refers to multi-dimensional data composed of discrete image elements (e.g., pixels for 2-D images and voxels for 3-D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R or $R^7$, the methods of the disclosures are not limited to such images, and can be applied to images of any dimension, e.g., a 2-D picture or a 3-D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

Figure 1:
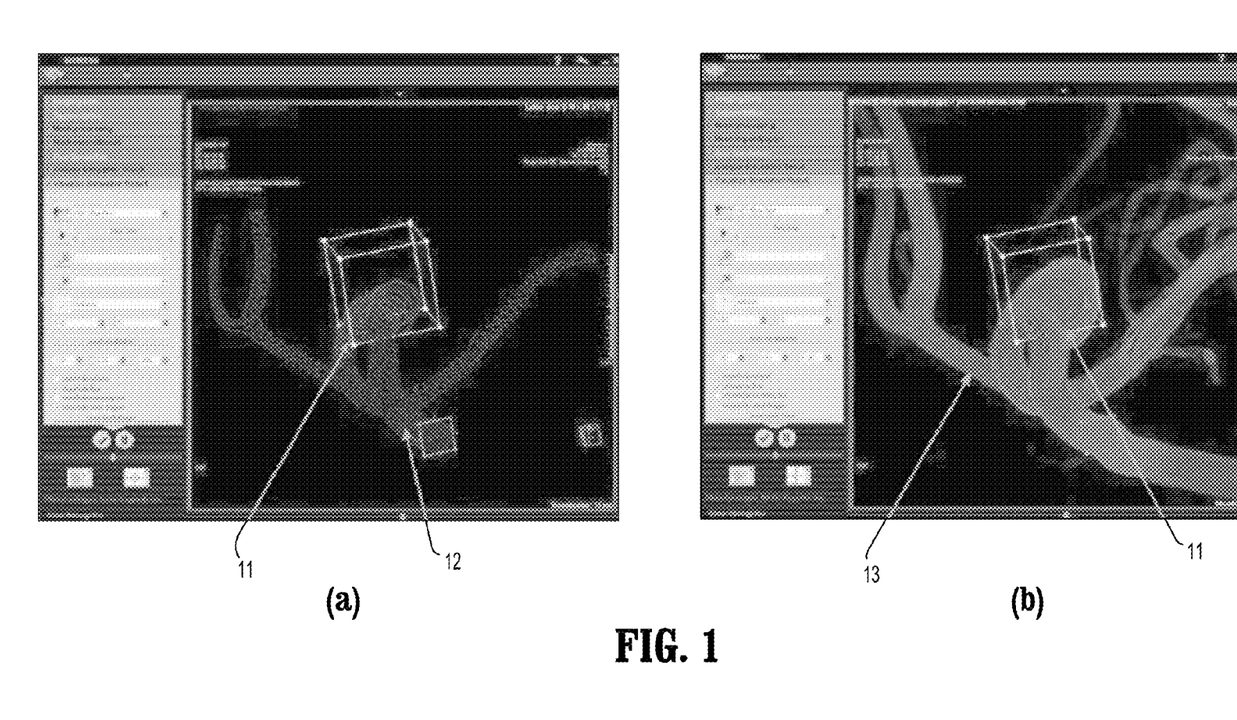
FIGS. 1(a)-(b) depicts a vessel flow field visualization using 3D particle traces, according to an embodiment of the disclosure.

Embodiments of the present disclosure introduce a novel method that visualizes and interacts with a vessel flow field from a web application, and can help users to explore the detail of a flow field. A 3D vessel flow image volume may contain multiple time steps and each time step may correspond to multiple vector/scalar fields. Typical image volume sizes are 108×60×84 or 45×63×78 voxels, however, other embodiments of the disclosure can process larger image volumes. Each volume may be evenly partitioned into data blocks. An exemplary, non-limiting block size is 3×3×3, however, larger block sizes may be used with larger image volumes, as long as the block can capture the overall structure of the vessels. The data blocks may be loaded on demand when a visualization program runs. Two look-up tables can be used to record the data loading status. The first look-up table is a mapping from a descriptor of the 3D image volume to an index that indicates the starting position in memory of the corresponding volume. An exemplary, non-limiting descriptor is a (time, property) name pair that identifies a time step and a particular vector/scalar field. The second look-up table indicates the memory position of each data block within the volume. In 3D vessel flow data, most data blocks do not contain any vessel structure, and these data blocks will not be loaded. Flow trajectories were displayed as 3D particle traces, as shown in FIGS. 1(a)-(b), which depicts vessel flow field visualization by 3D particle traces. FIG. 1(a) is a 3D perspective view through the image volume showing vessels 12 and a selection box 11, while FIG. 1(b) is a 2D volume rendering of the data 13 in FIG. 1(a), and also the selection box 11. The remaining data blocks are loaded into a graphics processing unit (GPU), which can map the 3D blocks into 2D sketches.

Figure 2:
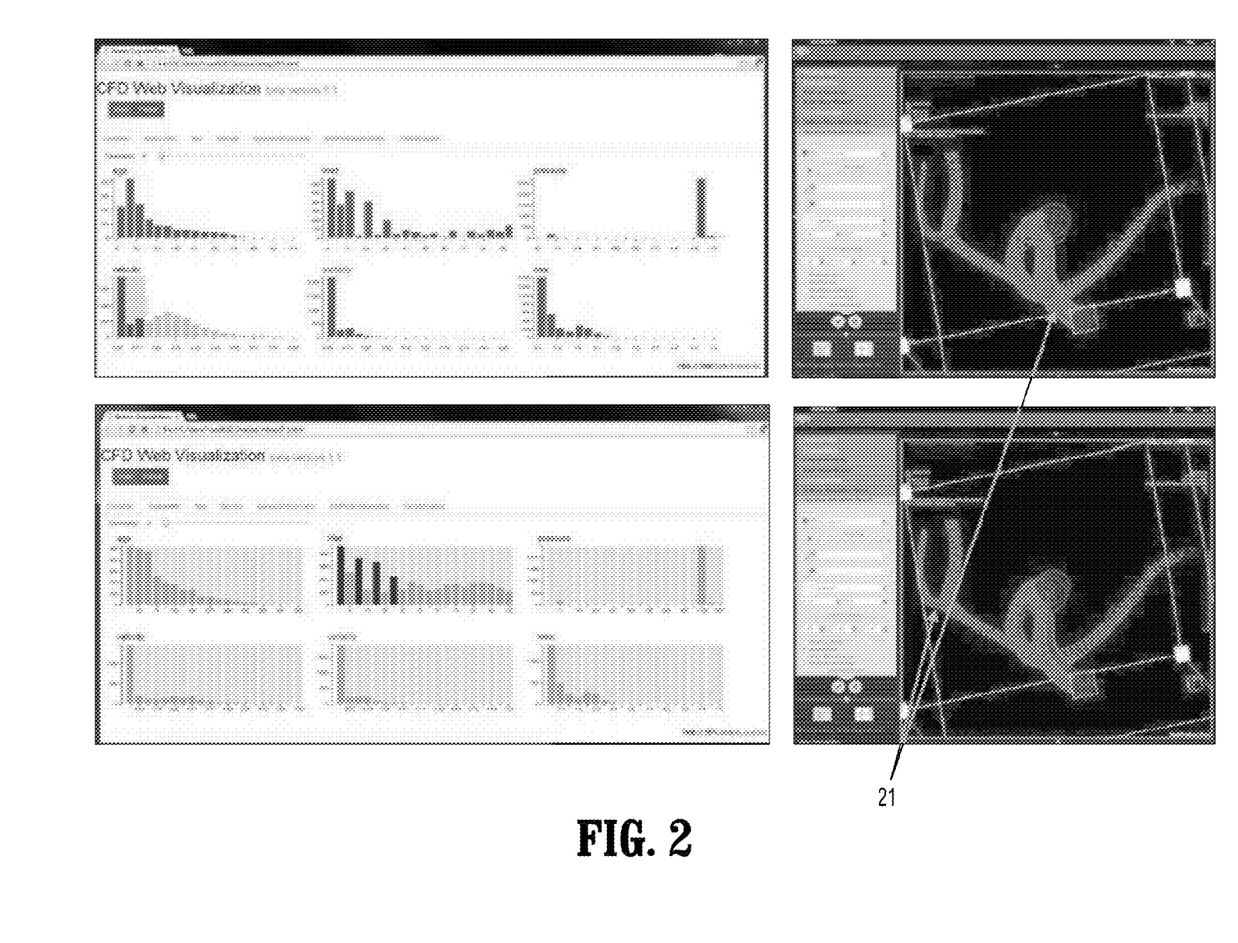
FIG. 2 illustrates an interface of a web application and the highlighting of particles in a CFD application, according to an embodiment of the disclosure.

According to an embodiment of the disclosure, the computation of statistical information of particles in the visualization may be implemented using OpenCL to utilize the parallelism of a graphics processing unit (GPU), where each thread is associated with a voxel. In this way, the removal of empty data blocks may also reduce the number of threads needed. The resulting information, which includes the group of selected particles themselves and statistical information about those particles, may then be copied from the GPU to the memory of a host computer. According to an embodiment of the disclosure, the host computer may compose the results in a data exchange format such as the JSON (JavaScript Object Notation) format and send it as a text string to the web front end. A method according to an embodiment of the disclosure can visualize in real-time statistical information of particles, such as velocity, voracity, wall shear stress, inlet and pressure. Here, inlet refers to a position in the flow field that is filled with fluid, such as blood in a vessel. In addition, a method according to an embodiment of the disclosure can query and highlight the particles in the flow field using a Cross filter and a Boolean filter, and the selected particles can be highlighted in a CFD application. Cross filter is a method of interacting with a histogram that allows users to drag and drop multi-sliders on the histograms to select a group of particles in a CFD application. The cross filter provides a convenient way for selecting a group of particles by multiple conditions. Boolean filter may be used in the same way. FIG. 2 illustrates an interface of a web application according to an embodiment of the disclosure and the highlighting of particles in a CFD application. In FIG. 2, the upper pair of images shows particles selected by a Cross filter, while the bottom pair of images show particles selected by a Boolean filter. For each pair, the left image visualizes statistical information of the selected particles, while the right image is the 2D volume rendering of the particles 21.

Figure 3:
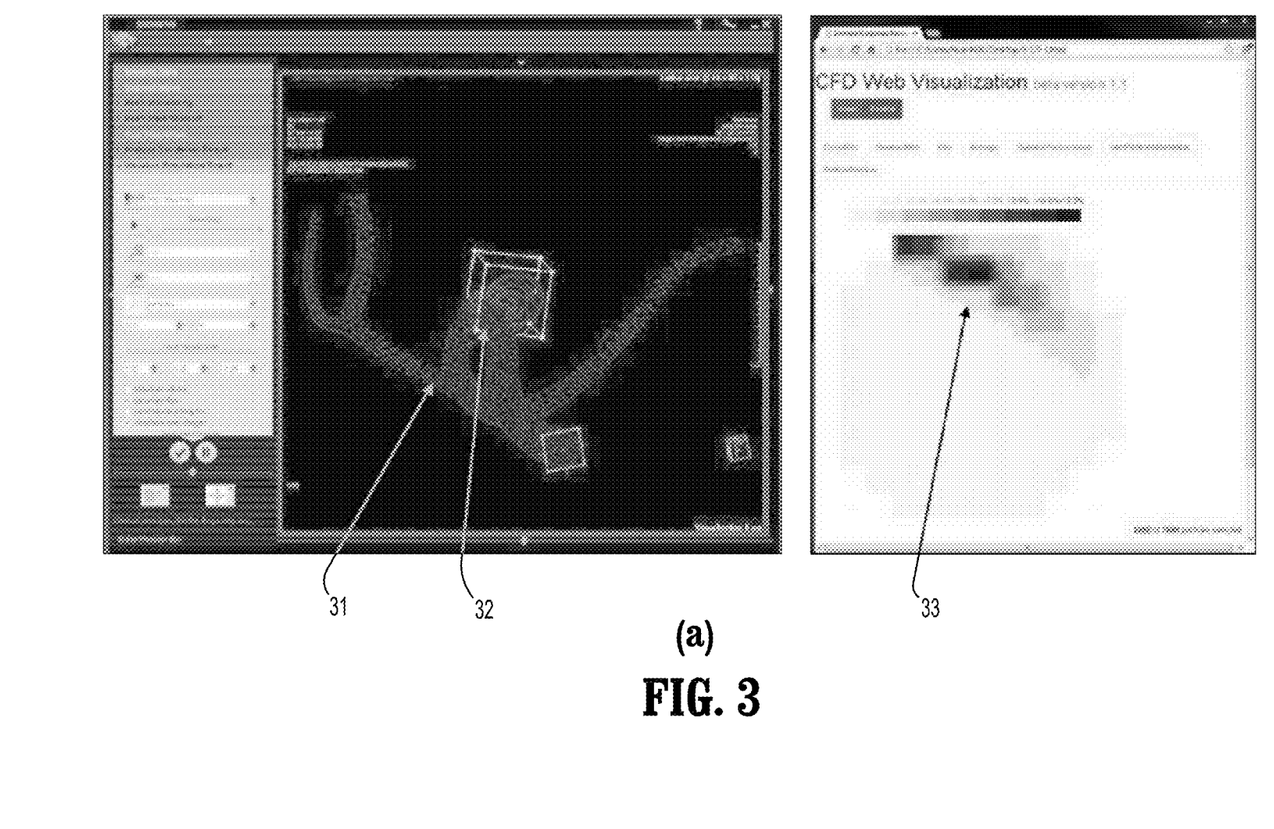
FIGS. 3(a)-(b) depict the contributing particle distribution at a flow inlet, according to an embodiment of the disclosure.
Figure 3B:
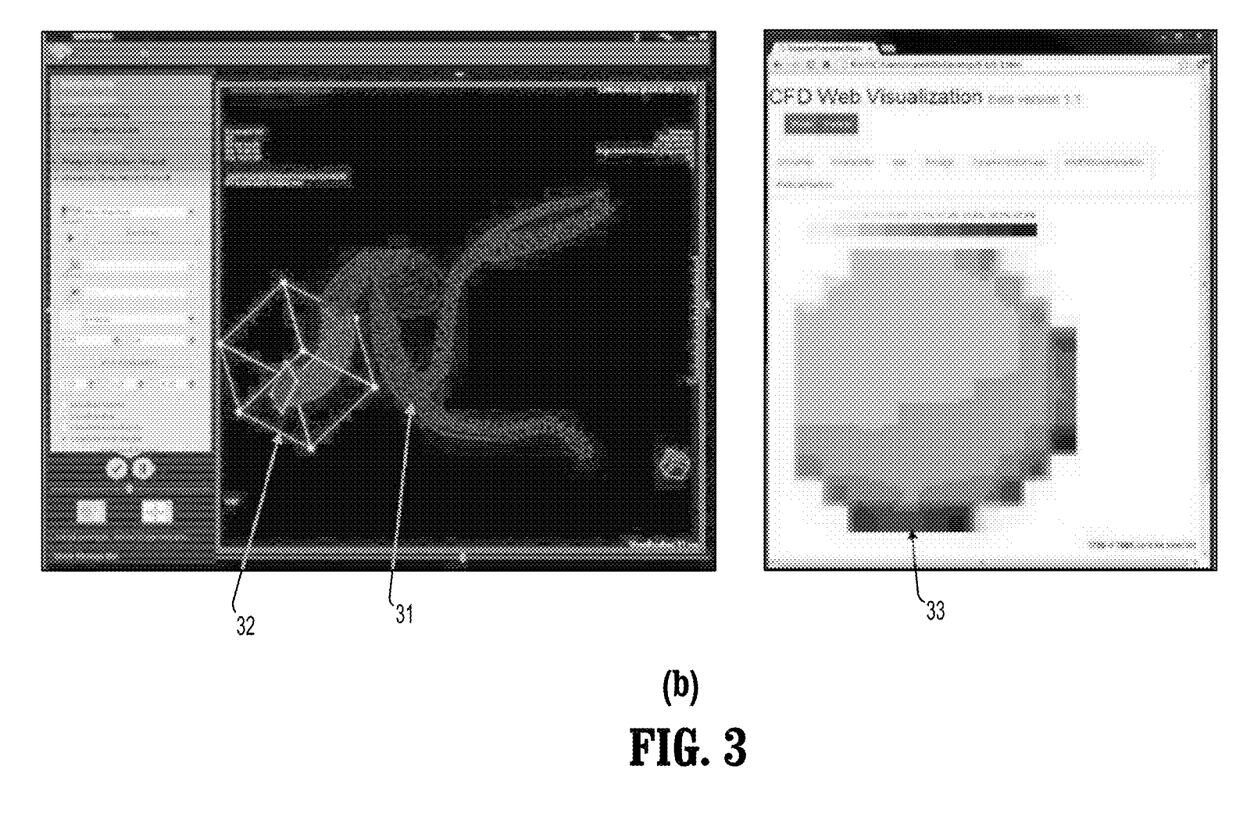
Figure 4:
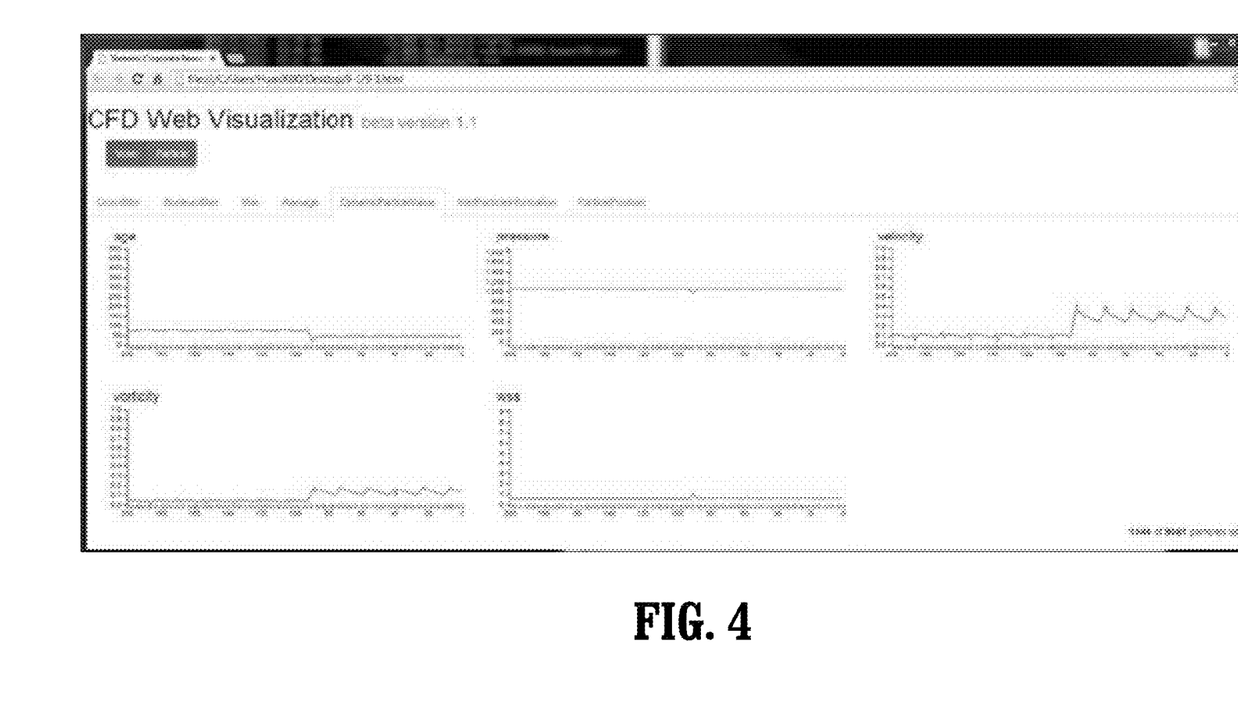
FIG. 4 shows real-time information visualization of particles in a region of interest, according to an embodiment of the disclosure.

FIGS. 3(a)-(b) depict the contributing particle distribution at a flow inlet. In FIG. 3, the upper pair of images shows particles selected by a Cross filter, while the bottom pair of images show particles selected by a Boolean filter. Each of FIGS. 3(a) and (b) show a 2D visualization of particles 31 with a selection box 32 in the left image, and an inlet heat map 32 in the right image of the particles selected by the drag box 33. All particles in each box are selected. As shown in FIGS. 3(a)-(b), users can drag and drop a selecting box to select a region of interest in a flow field. According to an embodiment of the disclosure, inlet information of the selected particle may be shown in a web application using a heat map. The color bar shows the percentage of particles of all selected particles in each inlet. FIG. 4 shows real-time information visualization of particles in a region of interest (ROI). The horizontal axis units in the graphs of FIG. 4 are the volume rendering time stamps. The information in the graphs includes age, which indicates how many time stamps in the volume rendering time after the particles came out from the inlet, pressure, velocity, voracity, and WSS (wall shear stress). As shown in FIG. 4, real-time information of the selected particles can be visualized in a CFD application. A CFD application according to an embodiment of the disclosure can show the mean of each feature of the selected particles, which can help users to find patterns in the particles of the ROI.

Figure 5:
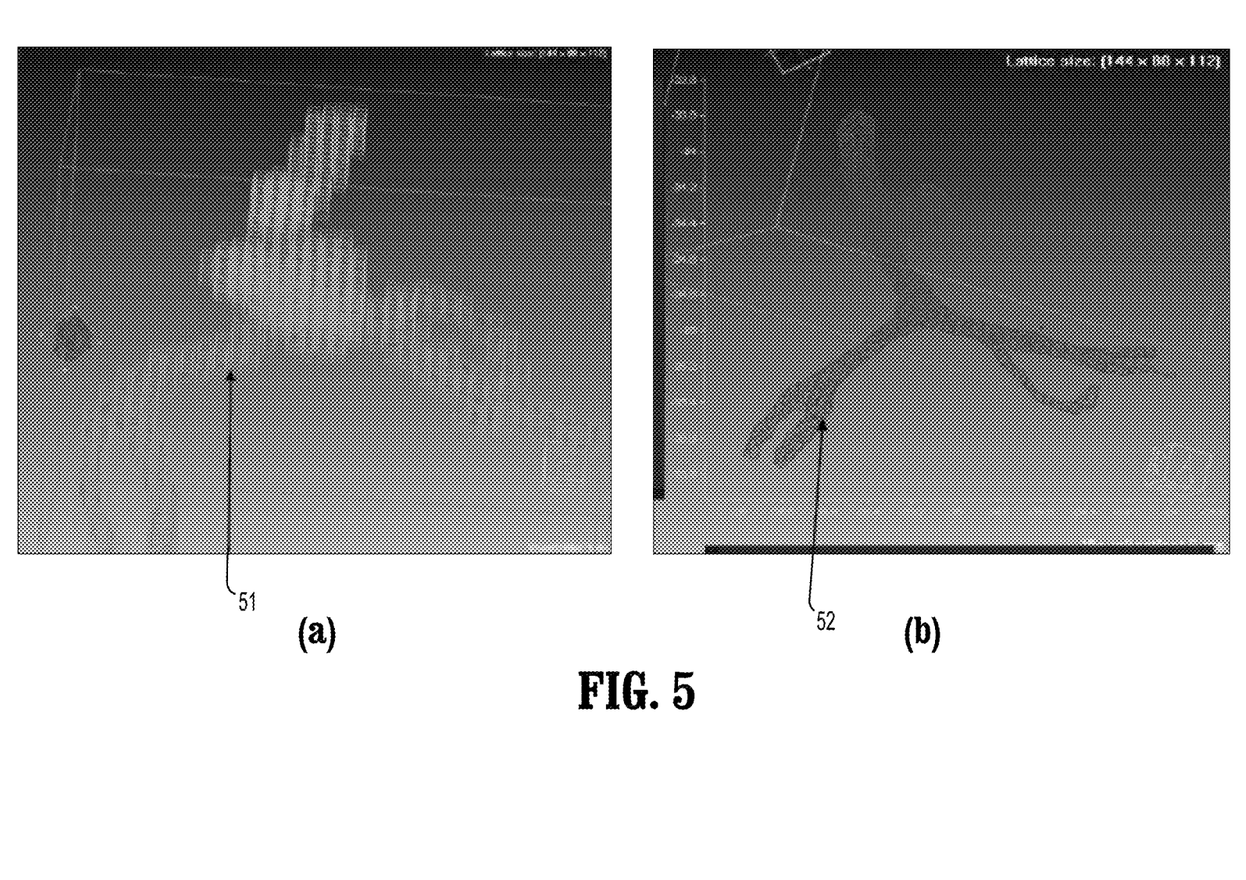
FIGS. 5(a)-(b) illustrates a mapping of 3D vessels data blocks to 2D vessel sketches that preserve the local shape of vessels, according to an embodiment of the disclosure.

FIGS. 5(a)-(b) illustrates a mapping of 3D vessels data blocks to 2D vessel sketches that preserve the local shape of vessels. According to an embodiment of the disclosure, the data blocks originally form a 3D grid structure 51, as shown in FIG. 5(a). Visualizing 3D volume information on web pages may be challenging, since the data blocks might occlude each other in 3D space and there may be a large amount of data to transfer. This may be even more challenging on a printed report, where rotations are not allowed.

According to an embodiment of the disclosure, the data blocks are mapped to a 2D visualization 52, as shown in FIG. 5(b), where the occlusions are eliminated. To build a connection between the original 3D volume and the 2D image, the mapping should preserve the local shape of vessels. According to an embodiment if the disclosure, the mapping can be formulated as a 2D graph layout optimization. Let the set of blocks that contain some of the vessel structure be B={$b_1$, $b_2$, . . . , $b_n$}. Then, the neighboring blocks of $b_i$ are those whose distances to $b_i$ are less than or equal to a given threshold d, and the non-neighboring blocks are those whose distances to $b_i$ are larger than d. The threshold d is used to determine whether a block is a neighboring block. Letting $v_i$ and $v_j$ be the 2D positions of $block_i$ and $block_j$, respectively, defining $|v_i-v_j|=t_{ij}$, where $t_{ij}$ is the target 2D distance, an interaction energy $E_{ij}$ can be expressed by $$E_{ij} = \begin{cases} W_n \times |t_{ij} - e_{ij}|, & e_{ij} < d, \\ W_{nn} \times |t_{ij} - g_{ij}|, & g_{ij} > d, \end{cases}$$

where $w_n$ and $w_{nn}$ are weights for neighboring and non-neighboring blocks, respectively, $t_{ij}$ is target distance between blocks $b_i$ and $b_j$ in 2D image, $e_{ij}$ is a Euclidean distance between them in the original 3D volume, and $g_{ij}$ is geodesic distance between them in the 3D vessel structure. Intuitively, for the neighboring blocks, their original distance are preserved to maintain the local shape of vessels; while for the non-neighboring ones, targeting the geodesic distance will separate two blocks in different vessel branch to avoid occlusion. The equations are composed as a matrix, so that a minimization can be performed by solving a linear system in least-squares sense to determine the 2D positions V of all blocks. Note that since the number of equations is much larger than the number of variables, the linear system is over-determined, which is why it is solved it in a least squares sense to minimize the sum $E=\sqrt{\Sigma_{ij}E_{ij}^2}$. Each term is weighted by one of the parameters $W_n$ and $W_{nn}$, which control the weights of energy between neighboring blocks and non-neighboring blocks, respectively. According to an embodiment of the disclosure, $W_n > W_{nn}$, which means the relationships between neighboring blocks are more important. The parameters $W_n$ and $W_{nn}$ are fixed during the minimization. According to an embodiment of the disclosure, the minimization is performed by varying the 2D positions $v_i$ and $v_j$ of the target blocks. This minimization may be implemented on a GPU.

Figure 6:
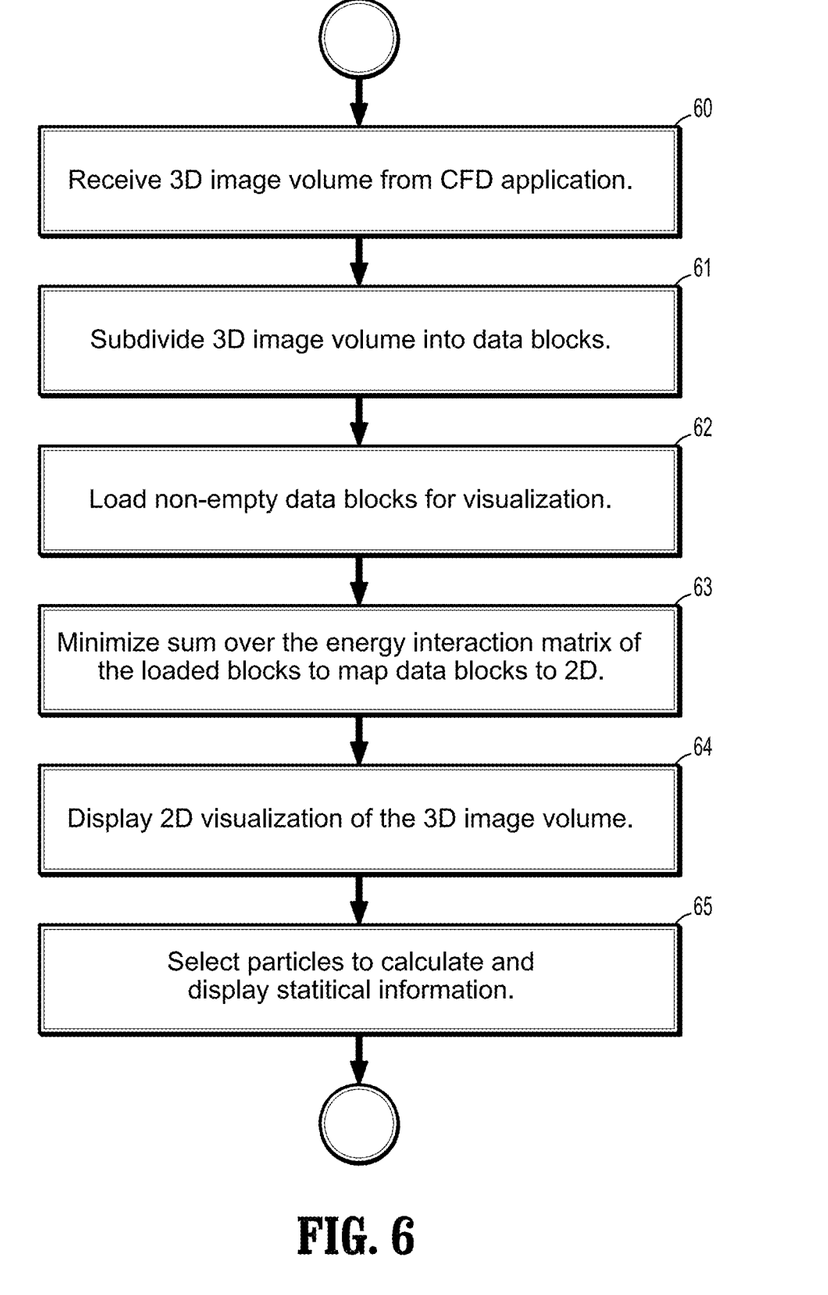
FIG. 6 is a flow chart of a method for a web based fast query visualization of a time-varying multi-variate vessel flow field, according to an embodiment of the disclosure.
Figure 7:
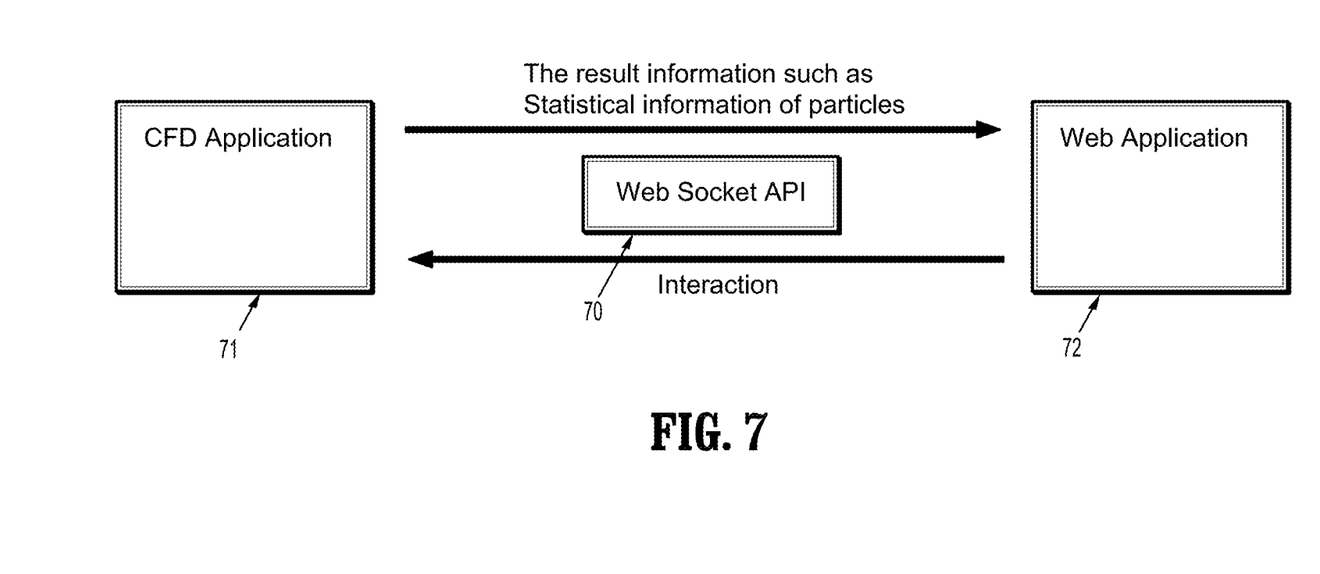
FIG. 7 is a block diagram of the structure of application according to an embodiment of the disclosure.

FIG. 6 is a flow chart of a method for a web based fast query visualization of a time-varying multi-variate vessel flow field, and FIG. 7 is a block is a block diagram of the structure of application according to an embodiment of the disclosure. FIG. 7 depicts a web application 72 according to an embodiment of the disclosure in signal communication with a CFD application 70 by means of a web socket API 71 running in a web browser. The CFD application 70 and a web application 72 according to an embodiment of the disclosure may run on the same computer, or they may run on different computers. Referring now to FIGS. 6 and 7, a method begins at step 60 by the web application 72 receiving a 3D image volume from the CFD application 70 that is a snapshot of a fluid dynamics simulation. The 3D snapshot would include a set of 3D positions and 3D velocity vectors that indicate the motion of the fluid and/or particles in the fluid. At step 61, the 3D image volume is subdivided into data blocks that are of a size suitable for loading into a web application according to an embodiment of the disclosure. At step 62, non-empty data blocks are loaded for visualization. At step 63, a sum over the energy interaction matrix of the loaded blocks, $E=\sqrt{\Sigma_{i,j} E_{i,j}{}^2}=\sqrt{\Sigma_{i,j} (AV-T)_{ij}{}^2}$ where $E_{ij}$ is as defined above, is minimized to define a mapping from the 3D data blocks to 2D. Once the energy has been minimized, a 2D mapping may be determined at step 64, and a 2D visualization of the 3D snapshot is displayed. In addition, once the visualization has been displayed, a user may select at step 65 a group of particles with a drag-and-drop selection box to calculate and display statistical information regarding the selected particles. As described above, the statistical information may include such as velocity, voracity, wall shear stress, inlet and pressure, and may be displayed in graphs such as those in FIG. 4.

It is to be understood that embodiments of the present disclosure can be implemented in various forms of hardware, software, firmware, special purpose processes, or a combination thereof. In one embodiment, the present disclosure can be implemented in software as an application program tangible embodied on a computer readable program storage device. The application program can be uploaded to, and executed by, a machine comprising any suitable architecture.

Figure 8:
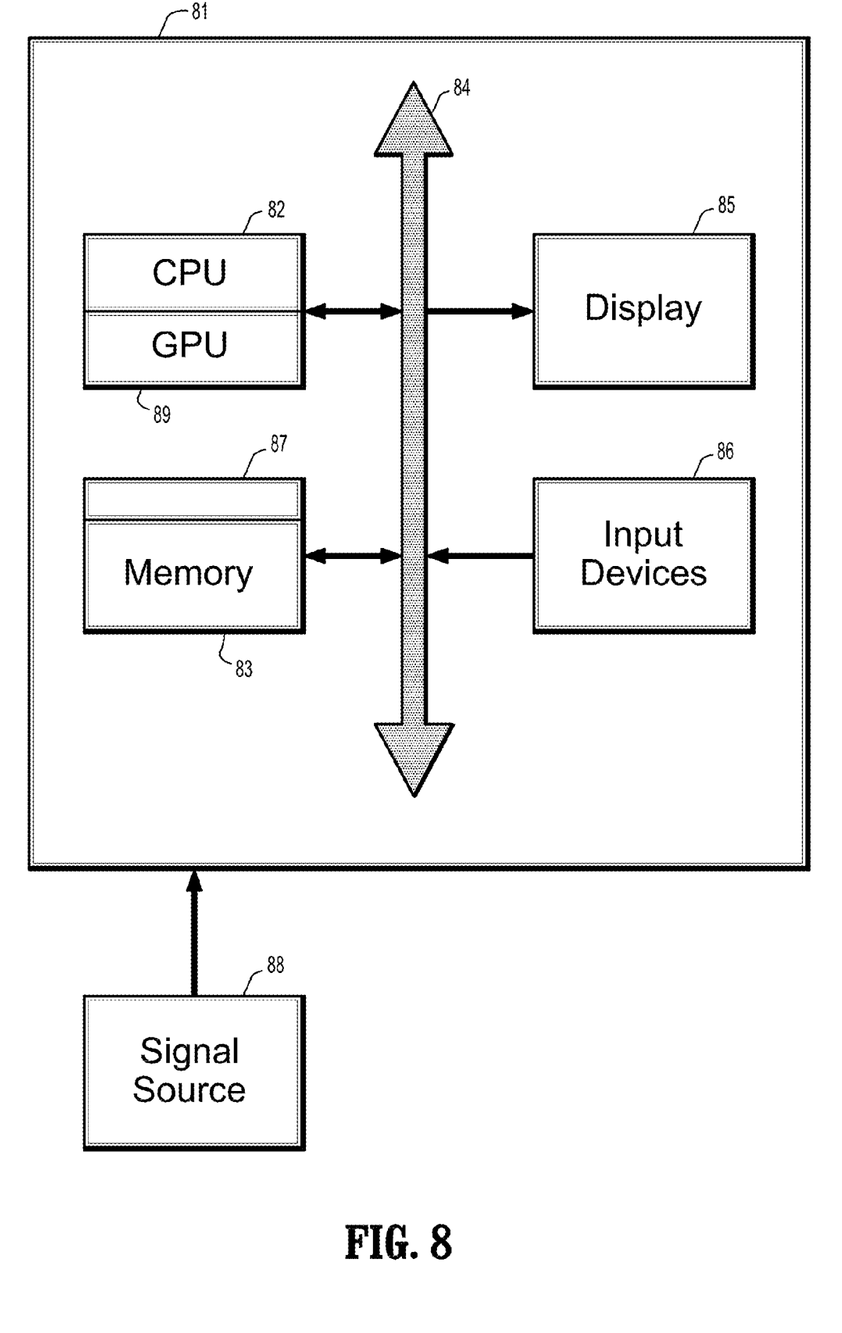
FIG. 8 is a block diagram of an exemplary computer system for implementing a method for a web based fast query visualization of a time-varying multi-variate vessel flow field, according to an embodiment of the disclosure.

FIG. 8 is a block diagram of an exemplary computer system for implementing a method for a web based fast query visualization of a time-varying multi-variate vessel flow field, according to an embodiment of the disclosure. Referring now to FIG. 8, a computer system 81 for implementing the present disclosure can comprise, inter alia, a central processing unit (CPU) 82, a graphics processing unit (GPU) 89, a memory 83 and an input/output (I/O) interface 84. The computer system 81 is generally coupled through the I/O interface 84 to a display 85 and various input devices 86 such as a mouse and a keyboard. The support circuits can include circuits such as cache, power supplies, clock circuits, and a communication bus. The memory 83 can include random access memory (RAM), read only memory (ROM), disk drive, tape drive, etc., or a combinations thereof. The present disclosure can be implemented as a routine 87 that is stored in memory 83 and executed by the CPU 82 to process the signal from the signal source 88. According to an embodiment of the disclosure, the signal source 88 may be a computational fluids dynamics application. As such, the computer system 81 is a general purpose computer system that becomes a specific purpose computer system when executing the routine 87 of the present disclosure.

The computer system 81 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present disclosure is programmed. Given the teachings of the present disclosure provided herein, one of ordinary skill in the related art will be able to contemplate these and similar implementations or configurations of the present disclosure.

While embodiments the present disclosure has been described in detail with reference to exemplary embodiments, those skilled in the art will appreciate that various modifications and substitutions can be made thereto without departing from the spirit and scope of the disclosure as set forth in the appended claims.

What is claimed is:

1. A method for visualizing flow data from computation fluid dynamics (CFD) applications in 2-dimensions (2D), comprising the steps of:

receiving a 3-dimensional (3D) image volume from a CFD simulation of fluids flowing through vessels in a patient that is a snapshot of a fluid flow in the vessels at a certain time;

subdividing the 3D image volume into 3D data blocks;

minimizing a sum over energy interactions defined for each pair of data blocks in the 3D image volume, wherein said minimization preserves a local shape of the vessels, wherein minimizing the sum over energy interactions is performed on a graphics processing unit (GPU), wherein minimizing the sum over the energy interactions comprises minimizing $E=\sqrt{\Sigma_{ij} E_{ij}{}^2}$ wherein $$E_{ij} = \begin{cases} W_n \times |t_{ij} - e_{ij}|, & e_{ij} < d, \\ W_{nn} \times |t_{ij} - g_{ij}|, & g_{ij} > d, \end{cases}$$

wherein $w_n$ and $w_{nn}$ are weights for neighboring and non-neighboring blocks, respectively, $t_{ij}=|v_i-v_j|$ is a target distance between blocks $b_i$ and $b_j$ in a 2D image wherein $v_i$ and $v_j$ are 2D positions of $b_i$ and $b_j$, $e_{ij}$ is a Euclidean distance between $b_i$ and $b_j$ in the 3D volume, $g_{ij}$ is a geodesic distance between $b_i$ and $b_j$ in the vessels in the 3D image, and d is a threshold that separates neighboring blocks from non-neighboring blocks, wherein the minimization is performed by varying the target positions $v_i$ and $v_j$; and using the minimized energy E to display on a monitor a 2D sketch of the 3D image volume, wherein the 2D sketch is displayed in real-time with respect to the time scale of the CFD simulation.

2. The method of claim 1, further comprising loading the 3D data blocks into memory of a web application for display, wherein the web application is accessible over the World Wide Web.

3. The method of claim 2, further comprising distinguishing non-empty 3D data blocks that contain vessels from empty 3D data blocks that do not contain vessels, and only loading the non-empty 3D data blocks.

4. The method of claim 3, further comprising calculating two look-up-tables (LUTs) when loading the non-empty data blocks, wherein an energy interaction is defined for each pair of non-empty data blocks.

5. The method of claim 4, wherein a first LUT is a mapping from a descriptor of the 3D image volume to an index that indicates a starting position in memory of the 3D image volume, and a second LUT indicates a memory position of each 3D data block of the image of the 3D image volume.

6. The method of claim 1, further comprising receiving a selection of particles selected from the 2D sketch, and calculating and displaying statistical information about the selected particles.

7. The method of claim 6, wherein the information includes one or more of velocity, vorticity, wall shear stress, inlet and pressure.

8. The method of claim 6, wherein the selection is performed using a Cross filter.

9. The method of claim 6, wherein the selection is performed using a Boolean filter.

10. The method of claim 1, wherein the vessels are at least a part of a cardiovascular system of the patient.

11. The method of claim 1, further comprising weighting each energy interaction $E_{ij}$ by a weight $W_n$ if a separation distance between $block_i$ and $block_j$ in 3D is less than the threshold distance d, and by a weight $W_{nn}$ if the separation distance between $block_i$ and $block_j$ in 3D is greater than or equal to the threshold distance d, wherein $W_n > W_{nn}$.

12. A non-transitory program storage device readable by a computer, tangibly embodying a program of instructions executed by the computer to perform the method steps for visualizing flow data from computation fluid dynamics (CFD) applications in 2-dimensions (2D), the method comprising the steps of:

receiving a 3-dimensional (3D) image volume from a CFD simulation of fluids flowing through vessels in a patient that is a snapshot of a fluid flow in the vessels at a certain time;

subdividing the 3D image volume into 3D data blocks;

minimizing a sum over energy interactions defined for each pair of data blocks in the 3D image volume, wherein said minimization preserves a local shape of the vessels, wherein minimizing the sum over energy interactions is performed on a graphics processing unit (GPU), wherein minimizing the sum over the energy interactions comprises minimizing $E = \sqrt{\Sigma_{ij} E_{ij}^2}$ wherein $$E_{ij} = \begin{cases} W_n \times |t_{ij} - e_{ij}|, & e_{ij} < d, \\ W_{nn} \times |t_{ij} - g_{ij}|, & g_{ij} > d, \end{cases}$$

wherein $w_n$ and $w_{nn}$ are weights for neighboring and non-neighboring blocks, respectively, $t_{ij} = |v_i - v_j|$ is a target distance between blocks $b_i$ and $b_j$ in a 2D image wherein $v_i$ and $v_j$ are 2D positions of $b_i$ and $b_j$, $e_{ij}$ is a Euclidean distance between $b_i$ and $b_j$ in the 3D volume, $g_{ij}$ is a geodesic distance between $b_i$ and $b_j$ in the vessels in the 3D image, and d is a threshold that separates neighboring blocks from non-neighboring blocks, wherein the minimization is performed by varying the target positions $v_i$ and $v_j$; and using the minimized energy E to display on a monitor a 2D sketch of the 3D image volume, wherein the 2D sketch is displayed in real-time with respect to the time scale of the CFD simulation.

13. The computer readable program storage device of claim 12, the method further comprising loading the 3D data blocks into memory of a web application for display, wherein the web application is accessible over the World Wide Web.

14. The computer readable program storage device of claim 13, the method further comprising distinguishing non-empty 3D data blocks that contain vessels from empty 3D data blocks that do not contain vessels, and only loading the non-empty 3D data blocks.

15. The computer readable program storage device of claim 14, the method further comprising calculating two look-up-tables (LUTs) when loading the non-empty data blocks, wherein an energy interaction is defined for each pair of non-empty data blocks.

16. The computer readable program storage device of claim 15, wherein a first LUT is a mapping from a descriptor of the 3D image volume to an index that indicates a starting position in memory of the 3D image volume, and a second LUT indicates a memory position of each 3D data block of the image of the 3D image volume.

17. The computer readable program storage device of claim 12, the method further comprising receiving a selection of particles selected from the 2D sketch, and calculating and displaying statistical information about the selected particles.

18. The computer readable program storage device of claim 17, wherein the information includes one or more of velocity, vorticity, wall shear stress, inlet and pressure.

19. The computer readable program storage device of claim 17, wherein the selection is performed using a Cross filter.

20. The computer readable program storage device of claim 17, wherein the selection is performed using a Boolean filter.

21. The computer readable program storage device of claim 12, wherein the vessels are at least a part of a cardiovascular system of the patient.

22. The computer readable program storage device of claim 12, the method further comprising weighting each energy interaction $E_{ij}$ by a weight $W_n$ if a separation distance between $block_i$ and $block_j$ in 3D is less than the threshold distance d, and by a weight $W_{nn}$ if the separation distance between $block_i$ and $block_j$ in 3D is greater than or equal to the threshold distance d, wherein $W_n > W_{nn}$.

* * * * *